United States Patent
Luo et al.

(10) Patent No.: US 10,533,220 B2
(45) Date of Patent: *Jan. 14, 2020

(54) DEVICE PREPARATION USING CONDENSED NUCLEIC ACID PARTICLES

(71) Applicant: LIFE TECHNOLOGIES CORPORATION, Carlsbad, CA (US)

(72) Inventors: Guobin Luo, Oceanside, CA (US); Marina Sedova, Foster City, CA (US); David Light, Branford, CT (US); Ryan Jones, Potomac, MD (US); Mohammad Alanjary, Escondido, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,579

(22) Filed: Oct. 17, 2017

(65) Prior Publication Data

US 2018/0223357 A1    Aug. 9, 2018

Related U.S. Application Data

(62) Division of application No. 14/485,282, filed on Sep. 12, 2014, now Pat. No. 9,797,011.

(60) Provisional application No. 62/020,292, filed on Jul. 2, 2014, provisional application No. 61/877,745, filed on Sep. 13, 2013.

(51) Int. Cl.
*C12Q 1/6874* (2018.01)
*C12Q 1/6806* (2018.01)

(52) U.S. Cl.
CPC .......... *C12Q 1/6874* (2013.01); *C12Q 1/6806* (2013.01)

(58) Field of Classification Search
CPC .......................... C12Q 1/6874; C12Q 1/6806
See application file for complete search history.

(56) References Cited

U.S. PATENT DOCUMENTS

| | | | |
|---|---|---|---|
| 4,485,224 A | 11/1984 | Smith | |
| 5,055,390 A | 10/1991 | Weaver et al. | |
| 5,478,893 A | 12/1995 | Ghosh et al. | |
| 5,720,928 A | 2/1998 | Schwartz | |
| 5,785,832 A | 7/1998 | Chiari et al. | |
| 5,830,658 A | 11/1998 | Gryaznov | |
| 5,932,711 A | 8/1999 | Boles et al. | |
| 6,180,770 B1 | 1/2001 | Boles et al. | |
| 6,372,813 B1 | 4/2002 | Johnson et al. | |
| 6,586,176 B1 | 7/2003 | Trnovsky et al. | |
| 6,656,725 B2 | 12/2003 | Mirzabekov et al. | |
| 9,797,011 B2 | 10/2017 | Luo et al. | |
| 2002/0047003 A1 | 4/2002 | Bedingham et al. | |
| 2007/0299249 A1 | 12/2007 | Songe | |
| 2008/0026373 A1 | 1/2008 | Rodionova | |
| 2008/0166727 A1 | 7/2008 | Esfandyarpour et al. | |
| 2009/0215635 A1 | 8/2009 | Carell et al. | |
| 2011/0077169 A1 | 3/2011 | McKernan et al. | |
| 2011/0306099 A1 | 12/2011 | Beasley et al. | |
| 2012/0171682 A1 | 7/2012 | Marchand et al. | |
| 2012/0322054 A1 | 12/2012 | Rothberg et al. | |
| 2013/0225421 A1 | 8/2013 | Li et al. | |

FOREIGN PATENT DOCUMENTS

| | | |
|---|---|---|
| CN | 1334871 A | 2/2002 |
| CN | 102884430 A | 1/2013 |
| CN | 103175866 A | 6/2013 |
| WO | WO-1999/021533 | 5/1999 |
| WO | WO-2001/008710 | 2/2001 |
| WO | WO-2011/047307 | 4/2011 |
| WO | WO-2012/024658 | 2/2012 |
| WO | WO-2012/129242 | 9/2012 |
| WO | WO-2013/066975 | 5/2013 |
| WO | WO-2014/013263 | 1/2014 |

OTHER PUBLICATIONS

Baumann et al., "Stretching of Single Collapsed DNA Molecules", *Biophysical Journal*, vol. 78, 2000, 1965-1978.
Holt, R et al., "The new paradigm of flow cell sequencing", *Genome Research*, vol. 18, 2008, 839-846.
Jarvie, "Next Generation Sequencing of Technologies", *Drug Discovery Today: Technologies*, vol. 2, No. 3, Elsevier, 2005, pp. 255-260.
Kombrabail, et al., "Flourescence Dynamics of DNA Condensed by the Molecular Crowding Agent Poly (Ethylene Glycol)", *Journal of Flourescence*, vol. 15, No. 5, Sep. 2005, 741-747.
Kornyshev et al., "Helical Structure Determines Different Susceptibilities of dsDNA, dsRNA, and tsDNA to Counterion-Induced Condensation", *Biophysical Journal*, vol. 104, May 2013, pp. 2031-2041.
Margulies, et al., "Genome sequencing in microfabricated high-density picolitre reactors", *Nature*, vol. 437, No. 15, Jul. 31, 2005, 376-380.
Margulies, et al., "Supplementary Methods for the article Genome Sequencing in Microfabricated High-Density Picolitre Reactors", *Nature*, vol. 437, No. 15, 2005, 1-34.
Merriman, et al., "Progress in ION Torrent semiconductor chip based sequencing", *Electrophoresis*, vol. 33, 2012, 3397-3417.
PCT/US2014/055485, International Search Report and Written Report of the International Searching Authority, dated Dec. 5, 2014, 12 pages.
PCT/US2015/038875, International Preliminary Report on Patentability, dated Jan. 12, 2017, 1-7.

(Continued)

*Primary Examiner* — Narayan K Bhat

(57) ABSTRACT

A method of sequencing a nucleic acid strand includes receiving particles having nucleic acid strands coupled to a polymer matrix, exposing the particles to a solution including a condensing agent, and applying the particles to a surface, the particles depositing on the surface.

19 Claims, 6 Drawing Sheets

(56) References Cited

OTHER PUBLICATIONS

PCT/US2015/038875, International Search Report and Written Opinion of the International Searching Authority, dated Oct. 5, 2015, 1-8.
Roche, "454 Sequencing", Sequencing Method Manual, 2010, 1-20.
Xu, "Next-Generation Sequencing for Biomedical Applications", Thesis. The University of New Mexico, Jul. 1, 2013, 1-234.

DEVICE PREPARATION USING CONDENSED NUCLEIC ACID PARTICLES

CROSS-REFERENCE TO RELATED APPLICATION(S)

This application is a division of U.S. application Ser. No. 14/485,282 filed Sep. 12, 2014, and claims priority to U.S. application No. 62/020,292 filed Jul. 2, 2014, and U.S. application No. 61/877,745 filed Sep. 13, 2013, which disclosures are herein incorporated by reference in their entirety.

FIELD OF THE DISCLOSURE

This disclosure, in general, relates to systems and methods for preparing devices for use in nucleic acid sequencing, particularly such devices that utilize nucleic acid containing particles.

BACKGROUND

Sequencing of nucleic acid strands, particularly DNA, has become increasingly important in advancing fields including medicine, agriculture, and biological research. However, conventional gel techniques for sequencing nucleic acid strands have proven time-consuming and expensive. More recent developments rely on the deposition of nucleic acid containing samples on substrates. Depending upon the sequencing technique, the sequence of the nucleic acid sample can be determined by measuring ionic responses to nucleic acid addition or by measuring fluorescent emissions resulting from nucleic acid addition.

However, such techniques that rely on the deposition of nucleic acid samples on a substrate suffer from deficiencies caused by a failure of some nucleic acid strands to bind to the surface of the substrate or caused by strands binding in close proximity to each other. Such deficiencies can lead to underutilization of the substrate, inaccurate data, lost or incomplete samples, or other inaccuracies.

As such, an improved system and method for preparing a sequencing device would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
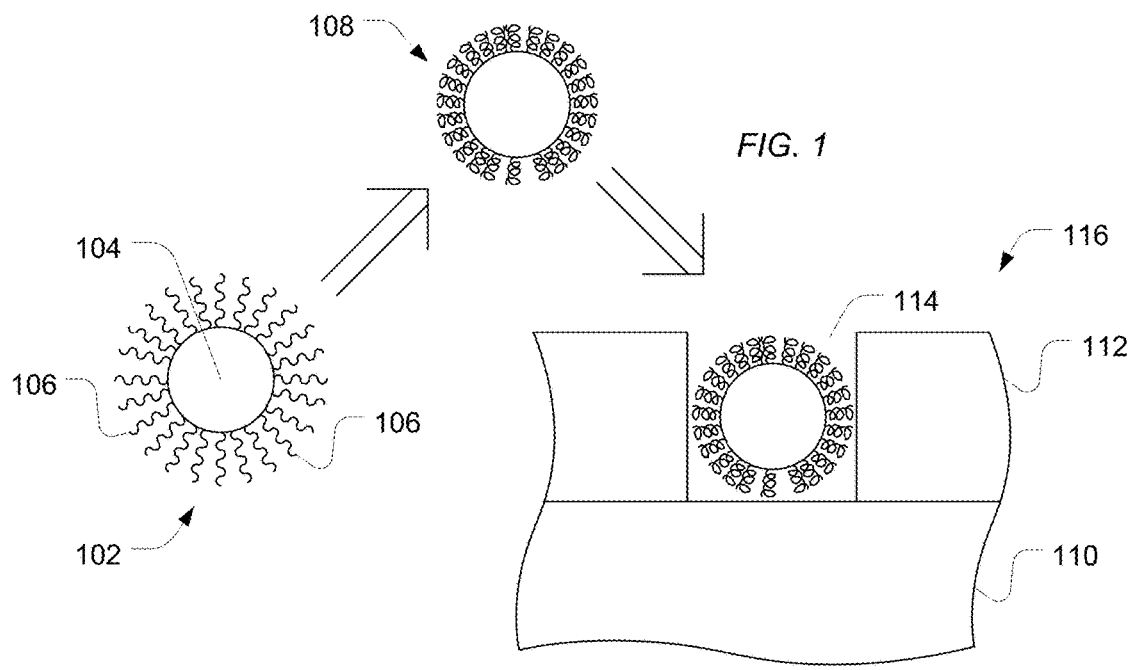
FIG. 1 includes an illustration of an exemplary method for depositing nucleic acid samples.

In an embodiment, a method includes preparing a nucleic acid bead or particle, condensing the nucleic acid bead, and depositing the condensed nucleic acid bead on a sensor substrate. In another example, the method includes depositing a nucleic acid bead on the sensor substrate and condensing the deposited nucleic acid bead. A nucleic acid bead or particle includes a bead conjugated to one or more nucleic acid strands. Condensing the nucleic acid bead can include condensing nucleic acids conjugated to the bead, shrinking the polymer of the bead, or a combination thereof, effectively reducing the size of the nucleic acid bead. After deposition, the condensed nucleic acid beads can be washed, which can expand the condensed nucleic acid beads. Subsequently, the sensor substrate with the deposited nucleic acid beads can be used for nucleic acid testing, such as sequencing, for example, sequencing-by-synthesis. Condensing the nucleic acid bead or particle can include exposing the nucleic acid bead or particle to a condensing agent. The condensing reagent can condense aspects of a nucleic acid bead or particle, for example, condensing the nucleic acid, the polymer matrix of the particle, or a combination thereof. In an example, the condensing agent includes a metal complex having a $3^+$ charge. For example, the metal complex can be a cobalt complex, such as a cobalt-amine complex. In another example, the condensing agent includes concentrated alkali or alkali-earth metal salts, such as a magnesium salt. In a further example, the condensing reagent includes a non-ionic polymeric reagent, such as a polyethylene glycol based reagent.

In another embodiment, a system implements a method for preparing a device for sequencing. The system can include a solution container, a sample receiving port or sample chamber, and a mixer coupled to the solution container and the sample receiving port or chamber. The mixer can be coupled to a substrate preparation unit. In an example, a solution in the solution container includes a condensing reagent including a condensing agent. Alternatively, the methods and processes described herein can be performed manually or with the use of stir plates, vortexers, pipettes, centrifuges, or other bench equipment.

The sample receiving port or sample chamber is to receive nucleic acid beads or particles, which have a polymeric matrix and a nucleic acid strand coupled to the polymeric matrix. The condensing reagent and the nucleic acid particles are mixed, such as in the mixer. As a result, the nucleic acid strand or the polymer matrix condenses, resulting in a particle with a reduced diameter or a greater density. The treated particles are transferred to a substrate preparation unit in which the particles are deposited on the substrate. In a particular example, the substrate includes a layer that defines wells, and the particles are deposited within wells. The substrate can be used for sequencing the nucleic acid strand of the bead or particle. In an example, the substrate is transferred to a sequencing device which performs functions resulting in sequencing of the nucleic acid strand.

Alternatively, the nucleic acid beads can be applied to the sensor substrate and the condensing reagent applied over the sensor substrate after the nucleic acid beads are deposited. In a further example, the nucleic acid beads can be treated with condensing agent prior to deposition, deposited, washed, and treated with condensing agent following deposition and washing.

As illustrated in FIG. 1, a nucleic acid bead or particle 102 includes a polymer matrix 104 and nucleic acid strands 106. While the nucleic acid strands 102 are illustrated as extending from a surface of the polymer matrix 104, the polymer matrix 104 can be porous, for example a hydrogel, and the nucleic acid strands 102 can be coupled to and extend throughout the polymer matrix 104. The nucleic acid beads or particles 102 can be treated to form treated nucleic acid beads or particles 108. The treated nucleic acid particle 108 can have a smaller diameter than the nucleic acid particle 102.

A surface component 116 includes a substrate 110, which includes a layer 112 that defines wells 114. The treated nucleic acid particle 108 can be deposited in the well 114. Subsequently, the treated nucleic acid particle 108 can be washed while it remains in the well 114. Washing can result in a nucleic acid particle with an increased diameter. Sequencing or other experimentation can be performed using the nucleic acid bead or particle while it remains in the well 114.

In an example, the nucleic acid beads or particles 102 include the polymer matrix 104 and one or more nucleic acid strands 106 coupled to the polymer matrix 104. The polymer matrix 104 can be formed of a hydrophobic polymer or can be formed of a hydrophilic polymer, such as a hydrogel matrix. In particular, the polymer matrix 104 can include a polymer, such as a polysaccharide such as agarose, hyaluronan, or methylcellulose; a polyoxyolefin such as polyoxybutylene, polyoxyethylene or polyethylene glycol, or polyoxypropylene; an acrylamide such as dimethylacrylamide, polyacrylamide, N,N-polydimethylacrylamide, poly(N-isopropylacrylamide), poly-N-hydroxyacrylamide, poly-N-hydroxyalkylacrylamide, or amine functional variants thereof; polyvinylpyrrolidone; polystyrene; silicone; poly(2-acrylamido-2-methyl-1-propanesulfonic acid); other acrylate polymers; polyvinyl alcohol; copolymers or derivatives thereof; or any combination thereof. In a particular example, the polymer matrix 104 can be formed of polystyrene. In another example, the polymer matrix 104 is formed of polyoxyethylene. In a further example, the polymer matrix 104 is formed of an acrylamide, such as hydroxyalkylacrylamide, amine terminated acrylamide, or a derivative thereof.

For example, the polymer matrix 104 can be formed from monomers including a radically polymerizable monomer, such as a vinyl-based monomer. In an example, the monomer can include acrylamide, vinyl acetate, hydroxyalkylmethacrylate, or any combination thereof. In a particular example, the hydrophilic monomer is an acrylamide, such as an acrylamide including hydroxyl terminal groups, amino terminal groups, carboxyl terminal groups, or a combination thereof. In an example, the hydrophilic monomer is an aminoalkyl acrylamide, an acrylamide functionalized with an amine terminated polypropylene glycol (D, illustrated below), an acrylopiperazine (C, illustrated below), or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide (A, illustrated below), N-(hydroxymethyl)acrylamide (B, illustrated below), or a combination thereof. In a further example, a mixture of monomers, such as a mixture of hydroxyalkyl acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1.

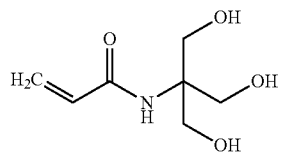  A

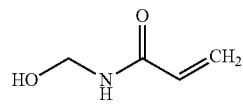  B

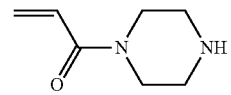  C

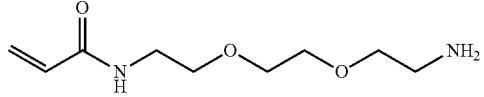  D

In a particular example, the polymer matrix 104 is a hydrogel bead substrate.

The polymer matrix 104 can include coupling sites to which a template polynucleotide can hybridize. The couplings sites can include the terminal groups, such as hydroxyl or amine terminal groups. For example, the coupling sites can each include a coupling oligonucleotide complementary to a section of a template polynucleotide. The template polynucleotide can include the target polynucleotide or segments complementary to the target polynucleotide, in addition to segments complementary to the coupling oligonucleotide.

The coupling oligonucleotide can be conjugated to the polymer matrix 104. The polymer of a polymer matrix 104 can be activated to facilitate conjugation with a target analyte, such as an oligonucleotide or polynucleotide. For example, functional groups on the polymer matrix 104 can be enhanced to permit binding with target analytes or analyte receptors. In a particular example, functional groups of the hydrophilic polymer can be modified with reagents capable of converting the hydrophilic polymer functional groups to reactive moieties that can undergo nucleophilic or electrophilic substitution. For example, hydroxyl groups on the substrate can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate may further react with liberated chlorine to provide chlorinated groups that can be used in a process to conjugate the particles. In another example, amine groups on a substrate can be activated.

For example, target analyte or analyte receptors can bind to the hydrophilic polymer through nucleophilic substitution with the sulfonate group. In particular example, target analyte receptors terminated with a nucleophile, such as an amine or a thiol, can undergo nucleophilic substitution to replace the sulfonate groups on the surface of the polymer matrix 104.

In another example, sulfonated polymer matrices can be further reacted with mono- or multi-functional mono- or multi-nucleophilic reagents that can form an attachment to the particle while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to oligonucleotides comprising nucleophilic groups.

In another example, a monomer containing the functional group can be added during the polymerization. The monomer can include, for example, an acrylamide containing a carboxylic acid, ester, halogen or other amine reactive group. The ester group may be hydrolyzed before the reaction with an amine terminated oligonucleotide.

Other conjugation techniques include the use of monomers that comprise amines. The amine is a nucleophilic group that can be further modified with amine reactive bi-functional bis-electrophilic reagents that yield a monofunctional electrophilic group subsequent to attachment to the bead or particle. Such an electrophilic group can be reacted with oligonucleotides having a nucleophilic group, such as an amine or thiol, causing attachment of the oligonucleotide by reaction with the vacant electrophile.

If the polymer matrix is prepared from a combination of amino- and hydroxyl-acrylamides, the substrate can include a combination of nucleophilic amino groups and neutral hydroxyl groups. The amino groups can be modified with di-functional bis-electrophilic moieties, such as a di-isocyanate or bis-NHS ester, resulting in a hydrophilic particle reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, a sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the particle via sulfonate activation. For example, reaction of sulfonated particles with thiobenzoic acid anion and hydrolysis of the consequent thiobenzoate incorporates a thiol into the particle which can be subsequently reacted with a maleimide substituted biomolecule to yield a thio-succinimide linkage to the biomolecule. Thiol can also be reacted with a bromo-acetyl group.

Alternatively, acrydite oligonucleotides can be used during the polymerization to incorporate oligonucleotides. An exemplary acrydite oligonucleotide can include an ion-exchanged oligonucleotides.

The polymer matrix 104 can have a diameter in a range of 0.1 μm to 15 μm. For example, the polymer matrix 104 can have a diameter in a range of 0.1 μm to 10 μm, such as a range of 0.1 μm to 5.0 μm, a range of 0.1 μm to 3.0 μm, or a range of 0.1 μm to 1 μm. In a particular example, the core 104 can have a diameter in a range of 0.1 μm to 0.8 μm, such as a range of 0.1 μm to 0.5 μm.

The nucleic acid strand 106 can have a length of at least 50 bases. For example, the nucleic acid strand can have a length of at least 100 bases. In a particular example, the nucleic acid strand can have a length between 100 and 10,000 bases, such as between 100 and 8,000 bases, between 100 and 5,000 bases, between 100 and 1,000 bases, or between 150 and 500 bases. The nucleic acid bead or particle 102 can include more than one nucleic acid strand bound to the polymer matrix 104. In a particular example, the nucleic acid strands on a nucleic acid particle are identical. For example, the particle can include at least 100, such as at least 1000, or even at least 10,000 identical copies of the nucleic acid strand. In particular, the nucleic acid particle 102 can include at least one 100,000 copies of the nucleic acid strand 106, such as at least 1 million copies of the nucleic acid strand. In an example, the nucleic acid particle 102 includes not greater than 100 million copies of the nucleic acid strand.

When mixed with a solution including a condensing agent, the nucleic acid strands or the polymer matrix condense. In an example, the condensing agent includes a metal-complex. The metal-complex can have $3^+$ charge and can be provided to the solution as a salt. For example, the metal complex salts can be a halide salts, such as a chloride salt or iodide salt. In particular, the metal complex includes cobalt, for example, forming a cobalt organic complex, such as a cobalt-amine complex. In an example, the metal-complex can include hexamine cobalt. In another example, the metal-complex includes tris(ethylenediamine) cobalt. In a further example, the metal complex includes cobalt sepulchate.

In particular, the solution can include the metal-complex in a concentration, such that when mixed with the sample, the concentration of the metal-complex in the resulting solution is at least 1 μM, such as at least 10 μM, at least 20 μM or at least 50 μM. In an example, the concentration can be in a range of 10 μM to 1 mM, such as a range of 20 μM to 500 μM, or even a range of 20 μM to 350 μM. In an alternative example, the concentration is at least 200 μM, such as at least 500 μM, or at least 1 mM. For example, the concentration can be at least 4.7 mM, such as at least 9.8 mM, at least 14.9 mM, or even at least 19.7 mM. In particular, the concentration is not greater than 100 mM, such as not greater than 50 mM. When expressed relative to the concentration of DNA, where the concentration of DNA is expressed in μg/ml, the ratio of the concentration of the metal-complex to the concentration of DNA is at least 0.5, such as at least 1.0, at least 1.5, at least 2.0, or even at least 3.0, but not greater than 100.

Alternatively or additionally, the solution can include a condensing agent that influences the density of the polymer matrix 104 of the bead or particle 102. For example, the solution can include an alcohol, such as methanol, ethanol or isopropyl alcohol (IPA), which can influence the density of the polymer matrix 104 of the particle 102. In particular, the solution can include an alcohol, such as methanol, in a concentration in a range of 0.1 vol. % to 60 vol. %, such as 0.1 vol. % to 50 vol. %, 0.1 vol. % to 30 vol. %, 0.1 vol. % to 20 vol. %, or even 0.1 vol. % to 10 vol. %. For example, the concentration of alcohol within the solution can be in a range of 0.1 vol. % to 5 vol. %, such as 1 vol. % to 5 vol. %. In another example, the solution can include an alcohol, such as ethanol or IPA in a concentration in a range of 0.1 vol. % to 60 vol. %, such as 1.0 vol. % to 60 vol. %, 5.0 vol. % to 60 vol. %, 10 vol. % to 60 vol. %, or even 40 vol. % to 60 vol. %.

In another example, the condensing agent includes concentrated alkali or alkali-earth metal salts, such as halide salts. In an additional example, the condensing agent can include magnesium chloride, for example, in a concentration in a range of 1 mM to 1M, such as a range of 30 mM to 1M, a range of 50 mM to 1M, a range of 50 mM to 800 mM, or even a range of 50 mM to 500 mM.

The condensing agent can further be a non-ionic polymer, such as a polyethylene glycol based polymer. In a particular example, the polyethylene glycol based polymer has a molecular weight in a range between 1000 Da and 100000 Da, such as a range between 2000 Da and 20000 Da, between 5000 Da and 15000 Da, or between 8000 Da and 12000 Da. The non-ionic polymer can be included in a concentration in a range of 0.1 wt % to 20.0 wt %, such as a range of 0.5 wt % to 15.0 wt %, a range of 0.5 wt % to 10 wt %, or a range of 2.5 wt % to 7.5 wt %.

The remainder of the solution can include a buffered solution, such as buffered saline solution. For example, the remainder of the solution can include a phosphate buffered saline solution. In particular, the solution can include sodium or potassium halide salts, sodium or potassium phosphate salts, and polysorbate. Such salts can be included, for example, in amounts in a range of 1 mM to 500 mM, such as 50 mM to 350 mM, or even 150 mM to 250 mM. In an example, potassium chloride can be included in a concentration in a range of 0.5 M to 2 M, such as a range of 0.8M to 1.5M, or even a range of 0.8M to 1.2M. In addition or alternatively, other buffering agents can be used, such as an amine based buffering agent, e.g., tris(hydroxymethyl)aminomethane. Such an amine buffering agent can be used in a concentration in a range of 50 mM to 1M, such as a range of 100 mM to 1M, a range of 100 mM to 800 mM, or even a range of 150 mM to 500 mM. Optionally, the solution can include other ionic components, such as calcium or magnesium, derived from salts. Further, the solution can have a pH between 6 and 9, such as between 6.5 and 8.5, or between 7 and 8.5.

The solution can include a surfactant. For example, the surfactant can be a non-ionic polymer surfactant, such as an ether of polyethylene glycol, for example an octylphenyl ether of polyethylene glycol. The non-ionic polymer surfactant can be included in a range of 0.01% to 1.0%, such as a range of 0.05% to 0.8%, a range of 0.05% to 0.5%, or even a range of 0.08% to 0.15%. An exemplary surfactant is TritonX-100.

In an example, a condensing solution includes a condensing agent, such as $MgCl_2$ in a range of 30 mM to 500 mM; a salt, such as KCl in a range of 0.8M to 1M; a buffering agent, such as tris(hydroxymethyl)aminomethane in a range of 150 mM to 500 mM; and a surfactant, such as TritonX-100 in a range of 0.05% to 0.5%. The pH is in a range of 7 to 9.

In another example, the condensing solution includes a combination of condensing agents, such as $MgCl_2$ in a range of 30 mM to 500 mM and polyethylene glycol in a range of 0.5 wt % to 10.0 wt %. The polyethylene glycol can have a molecular weight in a range of 5000 Da to 15000 Da. The condensing solution can also include a salt, such as KCl in a range of 0.8M to 1M; a buffering agent, such as tris (hydroxymethyl)aminomethane in a range of 150 mM to 500 mM; or a surfactant, such as TritonX-100 in a range of 0.05% to 0.5%. The pH is in a range of 7 to 9.

In response to exposure to the solution, the nucleic acid beads or particles 102 including the nucleic acid strands 106 can decrease in diameter. For example, the bead or particle diameter can decrease by at least 1% in response to exposure to the solution. In an example, the diameter decreases by at least 5%, such as at least 10%, at least 15%, or even at least 19%. In a particular example, the diameter decreases by not greater than 75%. Further, the density of the bead or particle can increase in response to exposure to a condensing agent. For example, the density can increase by at least 2%, such as at least 8%, at least 14%, at least 21%, or even at least 25%. In particular, the density increases by not greater than 75%.

Despite condensation of the nucleic acid strands 106 or the polymer matrix 104 in response to exposure to the condensing solution or reagent, the nucleic acid strands after exposure to the solution can exhibit a similar enzyme dissociation constant when compared to such a constant of the nucleic acid strands before exposure. For example, the nucleic acid strands after exposure can exhibit a similar dissociation constant when in the presence of a polymerase when compared with the nucleic acid strands before exposure.

Returning to FIG. 1, following exposure to the solution, the treated nucleic acid particles 108 can be applied to a surface component 116 of a sensor substrate, such as a sequencing device. For example, a suspension including the treated nucleic acid particles 108 can be applied over a surface of the surface component 116, such as by flowing the suspension across the surface, by foaming the suspension and applying the foam across the surface, or by applying the suspension and centrifuging the component 116. In a particular example, the surface includes regions to which the particles are secured, immobilized or bound. For example, the surface can include treated areas that are responsive to a surface agent on the beads or particles. In particular, the surface component 116 can include a pattern of treated areas, such as patterns of metal deposition.

In another example, the surface component 116 includes a layer 112 that defines wells 114 into which the treated nucleic acid beads or particles 108 can be deposited. Alternatively, the surface component 116 can include discrete sites, such as pits, grooves, channels, dimples, or other well-like sites. In a particular example, the surface component 116 can define wells 114 that correspond to active circuits for measuring ionic concentration, such as pH. Alternatively, the active circuits can measure, heat, fluorescence, or phosphate concentration. In another example, the wells 114 can be deposited over transparent layers of the surface component 116 for receiving or transferring electromagnetic radiation or fluorescent emissions.

The wells 114 can have an effective diameter of not greater than 10 μm, such as not greater than 7 μm, not greater than 4 μm, not greater than 3 μm, not greater than 2 μm, not greater than 1.5 μm, not greater than 1.0 μm, or even not greater than 0.8 μm. The effective diameter is the square root of the product of four times the cross-sectional area divided by pi (i.e., $d_{effective}=\text{sqrt}(4A/\pi)$). In particular, the effective diameter can be not greater than 1.0 μm or not greater than 0.8 μm. The effective diameter can be at least 0.3 μm. Further, the wells 114 can have a depth of not greater than 10 µm, such as not greater than 5 µm, not greater than 3 µm, not greater than 1.5 µm, or even not greater than 1 µm. For example, the depth can be not greater than 500 nm, such as not greater than 200 nm, or even not greater than 150 nm. The depth can be at least 100 nm.

The wells 114 can define a volume of not greater than 1 microliter, such as not greater than 100 nanoliters, not greater than 10 nanoliter, or not greater than 1 nanoliter. For example, the wells can define a volume of not greater than 100 picoliters, such as not greater than 10 picoliters, or even not greater than 1 picoliter. In particular, the wells can define a volume of not greater than 100 femtoliters, such as not greater than 50 femtoliters, such as not greater than 20 femtoliters, not greater than 10 femtoliters, not greater than 5 femtoliters, not greater than 1 femtoliter, or even not greater than 0.6 femtoliters, but can be at least 0.01 femtoliters.

Following deposition of the particles on surface, the surface component 116 can be placed in a sequencing system. Optionally, the surface component 116 can be washed to remove the condensing agent prior to placing it in the sequencing system or can be washed once placed in the sequencing system. In response, the nucleic acid bead or particle can increase in diameter or the nucleic acid strands can expand from a condensed state. For example, the beads or particles can be washed with a buffered solution, such as a buffered saline solution. In particular, the solution can be a solution similar to the condensing agent containing solution, absent the condensing agent.

Alternatively, the nucleic acid bead can be loaded before exposure to the condensing agent. For example, the nucleic acid beads can be applied to a sensor substrate and a solution including the condensing agent can be applied over the deposited nucleic acid beads. In a further alternative example, the nucleic acid bead can be treated with the condensing agent before depositing, deposited, washed, and treated with the condensing agent after being deposited.

Once placed in the sequencing system, the nucleic acid strands attached to the particles that are deposited on the surface component can be sequenced. In an example, sequencing can include measuring ion concentration in response to nucleotide addition. In such an example, a solution including a single type of nucleotide is contacted with the nucleic acid strands and the sequencing system monitors for changes in ion concentration, such as changes in pH. Subsequently, a solution with a different type of nucleotide can be applied to the surface and the ion concentration again monitored. In such a manner, the addition of individual nucleotides can be monitored and detected so as to determine which nucleotides are attached and in what order. In an alternative example, sequencing can include measuring fluorescent emissions in response to nucleotide addition. Nucleotides can be fed sequentially in separate solutions for each nucleotide or for nucleotides having a different fluorescent species, which fluoresce at different wavelengths, associated with each type of nucleotide, the nucleotides can be fed in a combined solution into the sequencing system.

Figure 2:
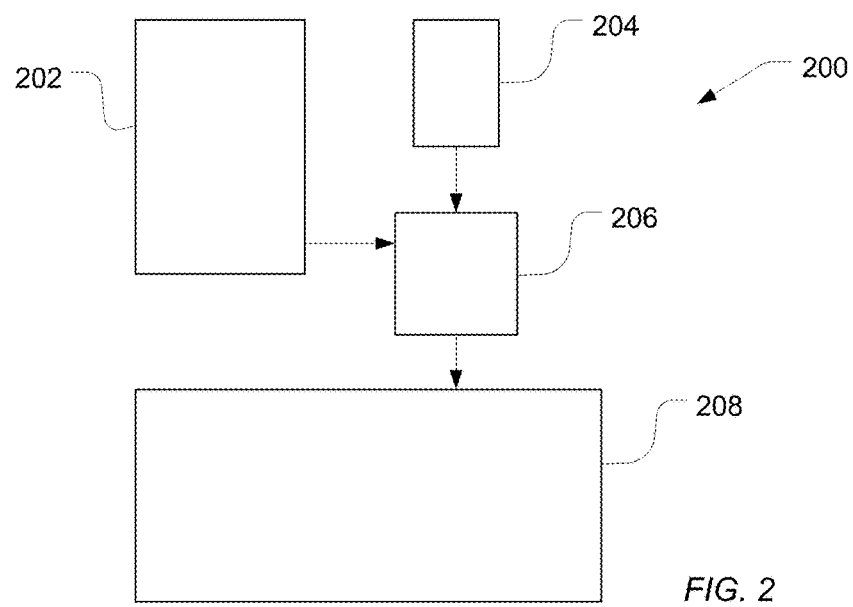
FIG. 2 includes an illustration of an exemplary device for preparing nucleic acid particles and preparing a device for sequencing.

Such a method can be implemented in a system, such as system 200 illustrated in FIG. 2. For example, the system 200 can include a solution container 202. Further, the system 200 includes a sample port or sample receiving chamber 204. Both the solution container 202 and the sample portal or receiving chamber 204 feed into a mixer 206. The mixer 206 can be an agitated mixer, an ultrasonic mixer, or an in-line mixer within tubing extending to a surface preparation unit 208. In particular, the mixing device 206 feeds treated particles received at the sample port or chamber 204 to a surface component to be prepared for use in the sequencing device. Alternatively, the solution container 202 and sample port or receiving chamber 204 can feed into the surface preparation unit 208 without entering a mixer or being mixed.

The surface preparation unit 208 can include a chamber in which the sensor substrate forms a major surface and through which the solution including a condensing agent and the nucleic acid beads or particles including nucleic acid strands flow across the surface to facilitate deposition of the beads or particles on the sensor substrate. In a particular example, the sensor substrate can include a flow cell defined over a sensor surface including wells. The surface preparation unit can further include agitators, aspirators, centrifuges, pipetters, or vortexers to further enhance deposition of the beads or particles into the wells of the sensor substrate. Alternatively, the process can be performed manually using the above equipment.

As a result of the method, the particles can be deposited on the surface component to a desirable surface density. For example, such a method can provide a surface component having an occupancy, defined as the percent of wells that include a DNA containing particle, of at least 60%, such as at least 80%, at least 85%, at least 87%, or even at least 89%. In particular, the occupancy can be at least 90%, such as at least 93%, or even at least 95%.

It is believed that an increase in density and a decrease in diameter assist with the concentrated deposition of particles on the surface. Following deposition, the particles can be washed either in the surface preparation device 208 or once placed in the sequencing system.

EXAMPLES

Example 1

Figure 3:
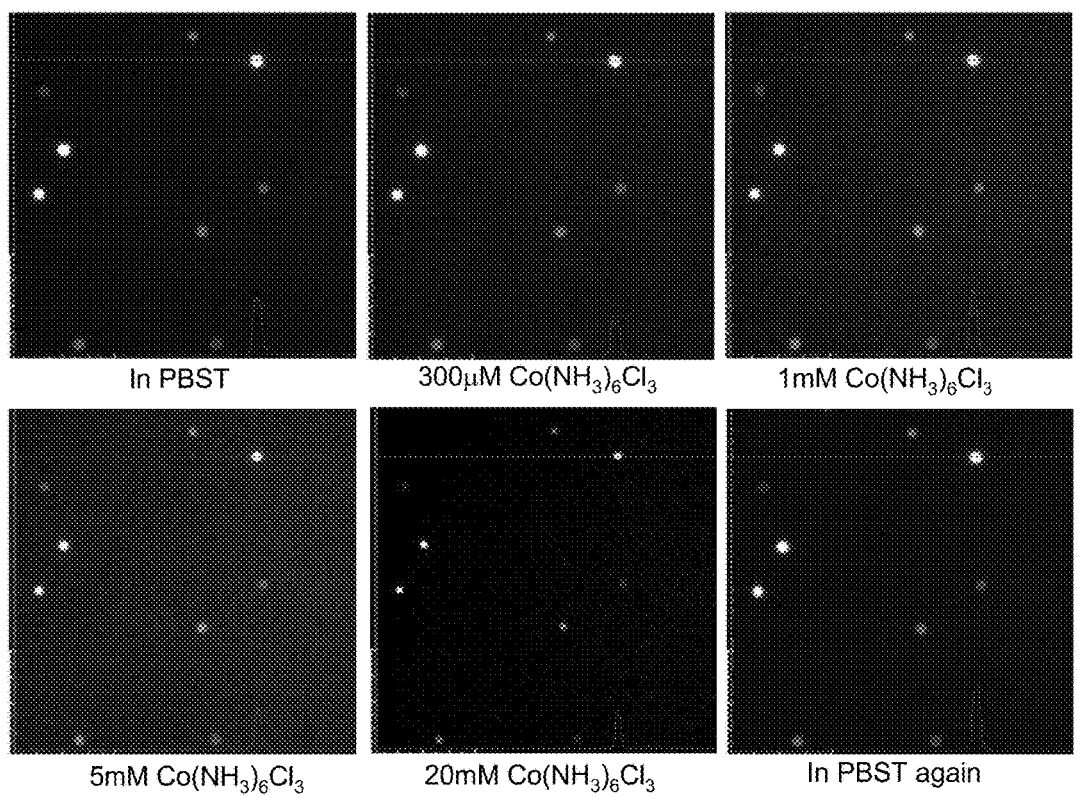
FIG. 3 includes images of beads or particles during exposure to hexamine cobalt.

Particles formed from DNA containing polymeric particles (ION Spheres™ following PCR amplification) are exposed to hexamine cobalt in concentrations ranging from 300 µM to 20 mM. FIG. 3 illustrates changes in particle diameter in response to changing concentration of hexamine cobalt. Initially, the particles are in a phosphate buffer saline with Tween-20 (PBST) solution (e.g., 1 liter aqueous solution including 8 g NaCl, 0.2 g KCl, 1.44 g $Na_2HPO_4$, 0.24 g $KH_2PO_4$, and 2 ml of tween-20). As the concentration of hexamine cobalt increases, the diameter of the particle decreases. The particle increases in diameter following washing with a PBST solution.

Figure 4:
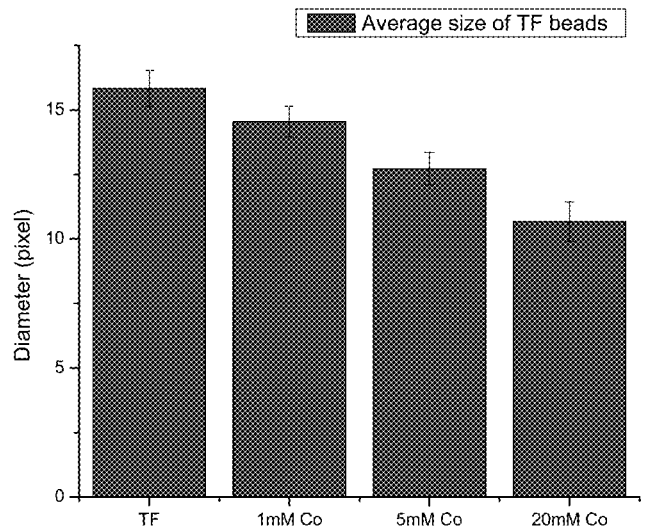
FIG. 4, FIG. 5, FIG. 6, FIG. 7, and FIG. 8 include graph illustrations of the size response of beads or particles to exposure to hexamine cobalt.
Figure 5:
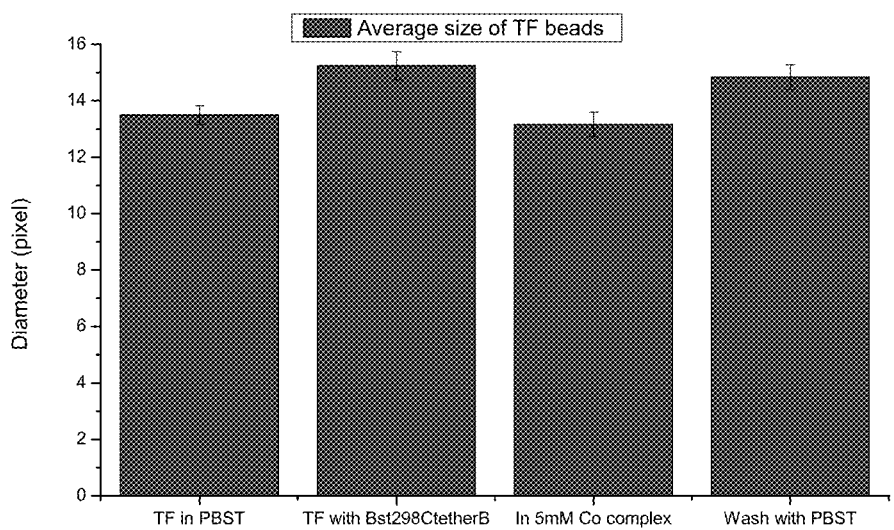

DNA containing particles are tested as prepared or in contact with polymerase enzyme. As illustrated in FIG. 4, the diameter of the DNA containing particles decrease with increasing concentration of hexamine cobalt. As illustrated in FIG. 5, the diameter increases when placed in contact with an enzyme. When the particle in contact with the enzyme is exposed to hexamine cobalt (5 mM Co-complex), the diameter decreases and subsequently increases when washed with a buffered solution (PBST).

Figure 6:
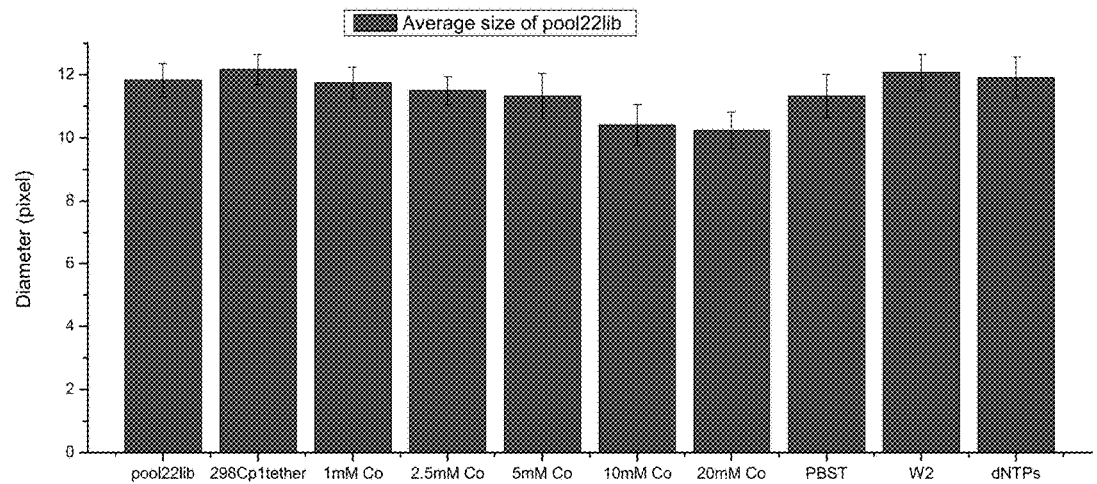
Figure 7:
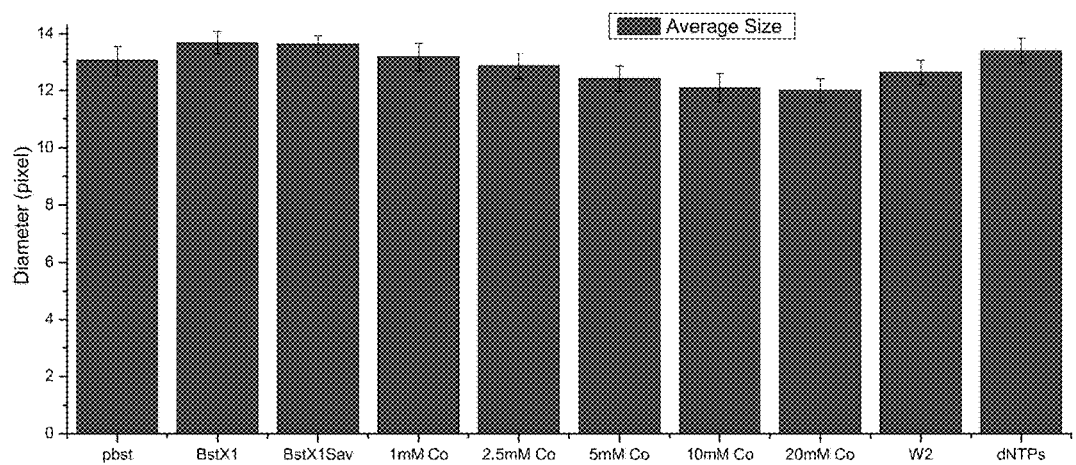
Figure 8:
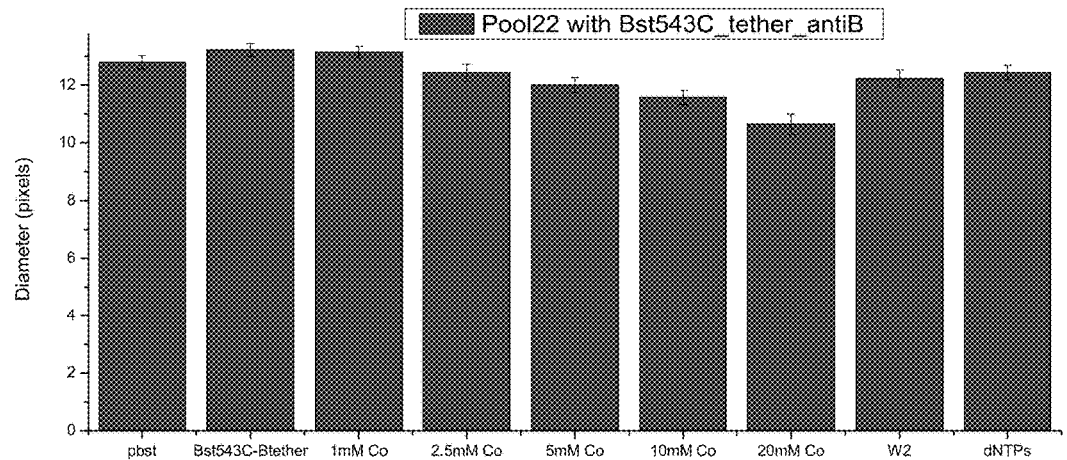

FIG. 6, FIG. 7, FIG. 8 illustrates the response of DNA containing particles formed using a nucleic acid library in contact with different enzymes. In each case, the diameter of the DNA containing particles increase when contacted with the enzyme and subsequently decreases in response to increasing concentrations of hexamine cobalt. Further, the diameter of the particles increases when washed first and second times with a buffered solution and when contacted with nucleic acid phosphates.

Figure 9:
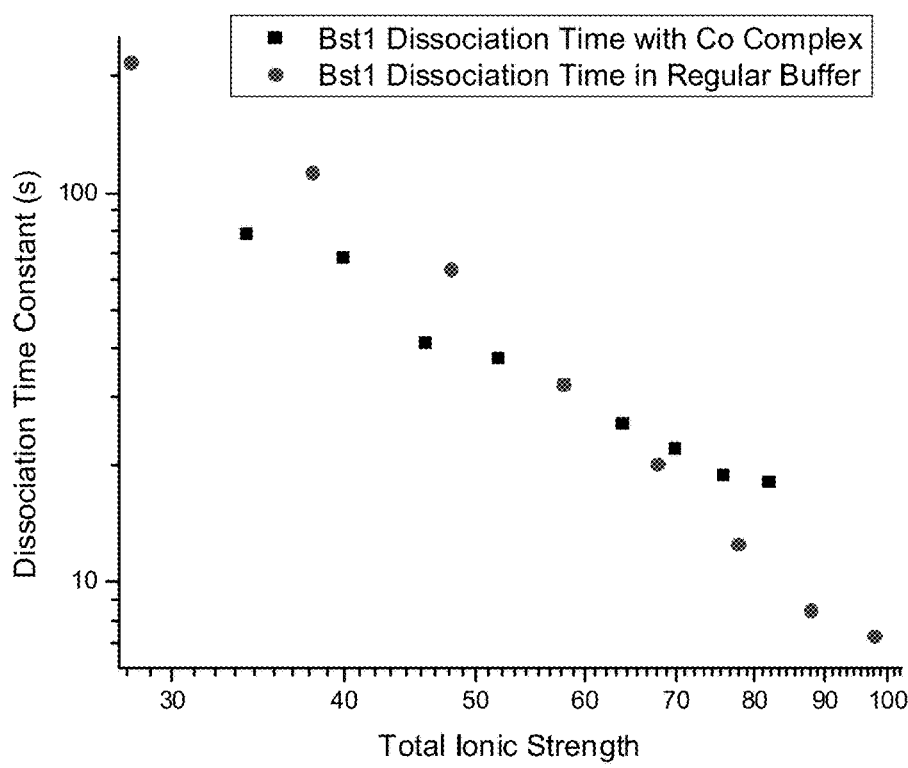
FIG. 9 includes a graph illustration of the dissociation kinetics of nucleic acid conjugated beads or particles both with and without exposure to hexamine cobalt.

Particles including FAM-labeled hairpins are tested to measure dissociation kinetics with an enzyme, Bst1. As illustrated in FIG. 9, the dissociation kinetics as a function of ionic strength is similar for samples exposed to hexamine cobalt and samples not exposed to hexamine cobalt.

DNA containing particles having an average core diameter of 0.7 microns are provided in both a suspension free of metal-complex and a suspension including hexamine cobalt. Substrates defining wells having an effective diameter of less than 1 micron are exposed to one of the two suspensions. The substrates are washed with a PBST solution and observed to determine how many of the wells are occupied with a DNA containing particle. Those substrates exposed to the suspension including DNA containing particles free of metal-complex exhibit an occupancy, defined as the percent of wells that include a DNA containing particle, of less than 60%. Those substrates exposed to the suspension including DNA containing particles and hexamine cobalt exhibit an occupancy of greater than 85%, some exhibiting an occupancy of greater than 90%.

Example 2

An aqueous condensing reagent can include 1M KCl, 230 mM $MgCl_2$, 200 mM tris-HCL, and 0.1% Triton X-100. The reagent can have a pH of approximately 8.0. When the condensing agent is used during loading of a polyacrylamide bead (available from Ion Torrent™) conjugated to polynucleotides onto a Proton I™ chip (available from ION Torrent™), it has been found that magnesium salt enhances loading of beads into wells. While not limiting the solution to a particular theory, it is believed that the solution causes condensation of a hydrogel polymer matrix.

Example 3

An aqueous condensing reagent includes condensing agents 100 mM $MgCl_2$ and 5 wt % polyethylene glycol. The polyethylene glycol has an average molecular weight of 10000 Da. The condensing solution also includes 0.7 M KCl and 200 mM tris(hydroxymethyl)aminomethane. The pH is 8.0.

Example 4

Hydrogel beads (ION Spheres™ available from ION Torrent) are treated with a coloring agent (SBYR) and are observed using microscopy for response to condensing agents including magnesium and polyethylene glycol (PEG). Bead size is expressed as a ratio relative to the bead size in a low ionic strength saline solution.

Figure 10:
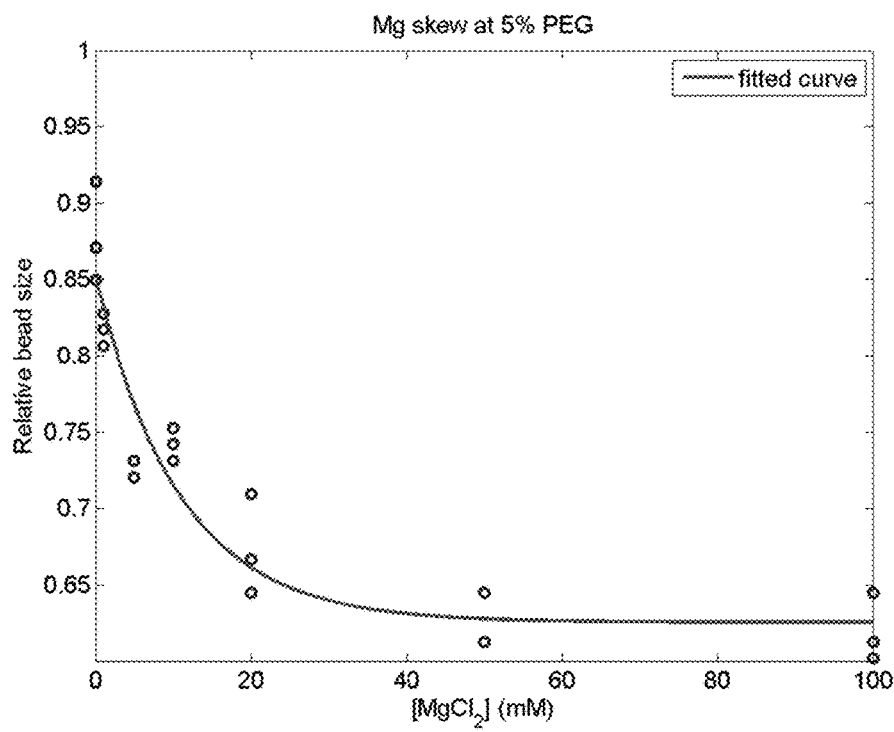
FIG. 10 and FIG. 11 include graph illustrations of the influence of condensing agents on bead size.

FIG. 10 illustrates the response of bead size to different concentrations of magnesium in the presence of 5% PEG. As illustrated, the relative size initially drops rapidly with increasing concentrations of magnesium. The rate of decrease slows with increasing concentrations of magnesium.

Figure 11:
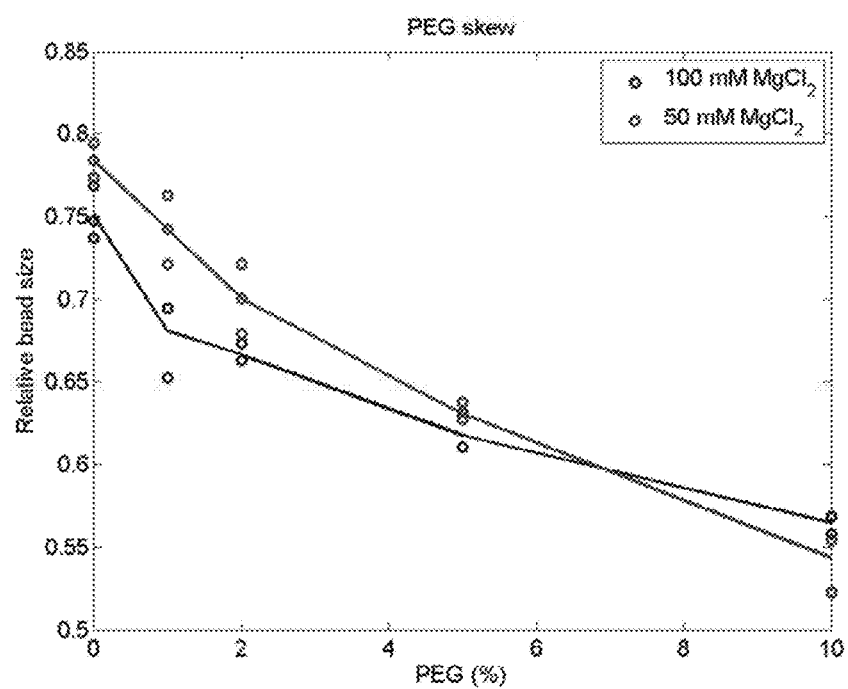

FIG. 11 illustrates the response of bead size to different concentrations of PEG, either in the presence of 100 mM $MgCl_2$ or 50 mM $MgCl_2$. As illustrated, the relative size decreases with increasing concentration of PEG. Polyethylene glycol may create a difference in osmotic pressure between the hydrogel bead and the external solution, causing water to exit the bead. The PEG may not enter the bead, but may remain external to the bead, leading to the difference in osmotic pressure.

In a first aspect, a method of sequencing a nucleic acid strand includes receiving particles having a polymer matrix conjugated to nucleic acid strands, exposing the particles to a solution including a condensing agent, and applying the particles to a surface, the particles depositing on the surface.

In an example of the first aspect, the condensing agent includes a metal complex having a 3+ charge. For example, the metal complex can include cobalt. In a further example of the first aspect and the above example, the metal complex is a metal-amine complex. For example, the metal complex can include hexamine cobalt. In another example, the metal complex includes tris(ethylenediamine) cobalt. In a further example, the metal complex includes cobalt sepulchrate. In an additional example, the metal complex is derived from a chloride salt. In an additional example of the first aspect and the above examples, the solution includes the metal complex in a concentration of at least 1 µM. For example, the concentration can be at least 10 µM, such as at least 1 mM, at least 4.7 mM, or even at least 14.9 mM. In particular, the concentration is not greater than 100 mM, such as not greater than 50 mM.

In a further example of the first aspect and the above examples, the surface includes a layer defining wells and wherein applying the particles to the surface includes applying the particles into the wells.

In another example of the first aspect and the above examples, the condensing agent includes a non-ionic polymer. For example, the non-ionic polymer includes a polyethylene glycol based polymer. The polyethylene glycol based polymer can have a molecular weight in a range of 2000 Da to 20000 Da. In an example, the non-ionic polymer surfactant is included in a concentration of 0.1% to 10.0% by weight.

In a further example, the condensing agent includes an alkali or alkali-earth salt. For example, the condensing agent includes a potassium salt in a concentration of 0.5M to 2.0M. In another example, the condensing agent includes a magnesium salt in a concentration of 30 mM to 1.0M.

In an additional example of the first aspect and the above examples, the condensing agent includes an alkali or alkali-earth metal salt and a non-ionic polymer surfactant.

In another example of the first aspect and the above examples, a diameter of the particle decreases by at least 1% in response to the exposure. For example, the diameter can decrease by at least 5%, such as at least 10%, at least 15%, or at least 19%. In particular, the diameter can decrease by not greater than 75%.

In a further example of the first aspect and the above examples, a density of the particles increases by at least 2% in response to the exposure. For example, the density can increase by at least 8%, such as at least 14%, or at least 21%. In particular, the density can increase by not greater than 75%.

In an additional example of the first aspect and the above examples, the nucleic acid strands exhibit a similar dissociation after exposure to the nucleic acid strands before exposure.

In another example of the first aspect and the above examples, the polymer matrix includes a polymer including agarose, polyoxybutylene, dimethylacrylamide, polyoxyethylene or polyethylene glycol, polyacrylamide, polyoxypropylene, N,N-polydimethylacrylamide, poly(N-isopropylacrylamide), polyvinylpyrrolidone, poly-N-hydroxyacrylamide, poly-N-hydroxyalkylacrylamide, polystyrene, copolymer or derivatives thereof, or any combination thereof.

In an additional example of the first aspect and the above examples, the method further includes washing the surface to remove the condensing agent.

In a further example of the first aspect and the above examples, the method further includes sequencing the nucleic acid strand. For example, sequencing can include measuring ion concentration in response to nucleotide addition. In another example, sequencing can include measuring radiation emissions in response to nucleotide addition.

In a second aspect, a method of preparing a surface includes applying a solution to a surface, the solution including particles and a condensing agent, the particles depositing onto the surface. The method also includes washing the surface with a solution free of the metal complex.

In a third aspect, a device includes a solution container including a solution including a condensing agent, a sample receiving port to receive particles including nucleic acid strands, and a mixer in fluid communication with the solution container and the sample receiving port.

In an example of the third aspect, the device further includes a surface preparation unit to prepare a surface component of a sequencing device and to receive treated particles from the mixer.

In a fourth aspect, an aqueous reagent solution includes a magnesium salt in a range of 30 mM to 500 mM; a potassium salt in a range of 0.8 M to 1.0 M; a buffering agent in a range of 150 mM to 500 mM; and a surfactant in a range of 0.05% to 0.5%.

In an example of the fourth aspect, the pH is in a range of 7 to 9. In another example of the fourth aspect and the above examples, the buffering agent includes tris(hydroxymethyl)aminomethane. In a further example of the fourth aspect and the above examples, the surfactant includes a polyethylene glycol based surfactant.

In a fifth aspect, an aqueous reagent solution includes a magnesium salt in a range of 30 mM to 500 mM; polyethylene glycol in a range of 0.5 wt % to 10.0 wt %; a potassium salt in a range of 0.8 M to 1.0 M; and a buffering agent in a range of 150 mM to 500 mM.

In an example of the fifth aspect, the pH is in a range of 7 to 9. In another example of the fifth aspect and the above examples, the buffering agent includes tris(hydroxymethyl)aminomethane.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of sequencing a nucleic acid strand, the method comprising:
   receiving a plurality of particles, a particle of the plurality of particles having a polymer matrix conjugated to a plurality of nucleic acid strands;
   exposing the plurality of particles to a solution including a condensing agent, wherein the nucleic acid strands condense in response to the condensing agent to form condensed particles having a reduced diameter, wherein a diameter of the particle decreases by at least 1% and not greater than 75% in response to the exposure;
   applying the plurality of condensed particles to a surface of a sequencing device, the surface defining a plurality of wells, the particles depositing into the wells on the surface; and
   washing the surface to remove the condensing agent from the condensed particles deposited in the wells, the condensed particles expanding and remaining in the wells.

2. The method of claim 1, wherein the condensing agent includes a metal complex having a 3+ charge.

3. The method of claim 2, wherein the metal complex comprises cobalt.

4. The method of claim 2, wherein the metal complex is a metal-amine complex.

5. The method of claim 2, wherein the metal complex includes hexamine cobalt.

6. The method of claim 2, wherein the solution includes the metal complex in a concentration of at least 1 µM.

7. The method of claim 1, wherein the condensing agent includes a non-ionic polymer.

8. The method of claim 7, wherein the non-ionic polymer includes a polyethylene glycol based polymer.

9. The method of claim 8, wherein the polyethylene glycol based polymer has a molecular weight in a range of 2000 to 20000.

10. The method of claim 7, wherein the non-ionic polymer is included in a concentration of 0.1% to 10.0% by weight.

11. The method of claim 1, wherein the condensing agent includes an alkali or alkali-earth salt.

12. The method of claim 11, wherein the condensing agent includes a magnesium salt in a concentration of 30 mM to 1.0M.

13. The method of claim 1, wherein the condensing agent includes an alkali or alkali-earth metal salt and a non-ionic polymer.

14. The method of claim 1, wherein the polymer matrix condenses in response to the condensing agent.

15. The method of claim 1, wherein a density of the particles increases by at least 2% and not greater than 75% in response to the exposure.

16. The method of claim 1, wherein the nucleic acid strands exhibit a similar dissociation after exposure to the nucleic acid strands before exposure.

17. The method of claim 1, wherein the polymer matrix comprises a polymer comprising agarose, polyoxybutylene, dimethylacrylamide, polyoxyethylene or polyethylene glycol, polyacrylamide, polyoxypropylene, N,N-polydimethylacrylamide, poly(N-isopropylacrylamide), polyvinylpyrrolidone, poly-N-hydroxyacrylamide, poly-N-hydroxyalkylacrylamide, or copolymers thereof.

18. The method of claim 1, further comprising: sequencing the nucleic acid strand.

19. The method of claim 1, further comprising a plurality of active circuits associated with the plurality of wells.

* * * * *